United States Patent [19]

Melman

[11] Patent Number: 5,480,658

[45] Date of Patent: Jan. 2, 1996

[54] EAR AND SKIN CLEANSER

[76] Inventor: Steven A. Melman, 8909 Iverleigh Ct., Potomac, Md. 20854

[21] Appl. No.: 96,715

[22] Filed: Jul. 23, 1993

[51] Int. Cl.$^6$ .................................................. A01N 59/14

[52] U.S. Cl. .............. 424/659; 252/182.12; 252/182.32; 514/578

[58] Field of Search ...................... 424/659; 252/182.12, 252/182.32; 514/578

[56] References Cited

PUBLICATIONS

Biological Abstracts 96:100793 1993.

*Primary Examiner*—Paul J. Killos
*Attorney, Agent, or Firm*—Evenson, McKeown, Edwards & Lenahan

[57] ABSTRACT

The present invention relates to a preferably pH balanced multi-purpose cleaning solution containing acetic acid and boric acid in a water base, useful on pets for the routine cleaning of the ear, the cleaning of the sensitive ear, particularly for cleaning moist, waxy or odiferous ears, the prevention and treatment of ear disease such as Swimmer's Ear and other ear diseases, acidification of the ear, and wound cleaning. The claimed solution may also contain a topical anesthetic, such as lidocaine hydrochloride, to provide relief from pain during treatment, and may be used as a carrier material for topical applications of medications including antibiotics and corticosteroids.

9 Claims, No Drawings

EAR AND SKIN CLEANSER

BACKGROUND OF THE INVENTION

The present invention relates to an acetic acid and boric acid multi-purpose cleansing solution for use on pets. Emphasis is on the usefulness of the solution for the routine cleaning of the ear, the cleaning of the sensitive ear, particularly for cleaning moist, waxy or odiferous ears, the prevention and treatment of ear disease, acidification of the ear, and wound cleaning. The solution may also be combined with a topical anesthetic to provide relief from pain caused by irritation, redness, swelling and lesions while the ear or skin is being treated. Additionally, the solution may be used as a carrier for topical applications of medications including corticosteroids and antibiotics.

Keeping pet's ears clean and free from infection and parasites has always been a problem for pet owners, groomers and veterinarians, partially because the structure of most pet ears do not allow access for cleaning, especially if the pet is uncooperative because of an already irritated ear. Additionally, as the structure of the ear canal of pets are convoluted and inverted and are not self-cleaning or draining, and naturally produce oils and lipids, or fatty acids, and wax, collectively called cerumen, they are prone to becoming irritated because of wax build-up, excessive moisture or yeast infections. Swimmer's Ear is an example of a common affectation of the ear caused by excessive moisture whereby a swimmer receives contaminated water in the ear or overly moisturizes (macerates) the ear causing it to succumb to microbial growth (most often pseudomonas).

Other factors present in certain breeds of dogs, such as hair in the ears (poodles, terriers), pendulous ears (spaniels), or narrow vertical canal and/or folded pinna (sharpei), further predisposes the ear to ear disease and increases the risk of ear disease.

Furthermore, in many cases of chronic ear disease, the tympanic membrane may be or have been ruptured, allowing infection into the middle ear and creating a cleansing and treatment dilemma since many cleansers and treatments are ototoxic.

Generally, substances that kill nerve cell s in the ear causing deafness and loss of equilibrium are ototoxic. Water and acetic acid in the ear causing a temporary vestibular effect are not. Aminoglycosides (gentamycin, amikacin, neomycin, tobramycin), erythromycin, chlorhexidine, and salicylates (including salicylic acid) are ototoxic and when combined may potentiate one another.

Oil or oil-like materials, such as mineral oil, are often used for cleaning pet ears and are helpful in eliminating ear mites. However, such solutions do not dissolve ear wax or kill yeast infections, they are not easily cleaned out of the ear once applied, and they are thick and do not evaporate, thereby leaving a residue coating the inner ear which in turn attracts dust and dirt particles and the like, causing further problems.

Alcohol is also commonly used to clean out the ear because it dissolves the natural oils and fats present in the ear, but alcohol is also irritating, especially if the ear is presented with lesions or is inflamed. Alcohol evaporates quickly, thereby often over-drying the ear and leaving it red and irritated.

Hydrogen peroxide is also often used to clean pet ears, but it does not dissolve the waxes and oils and does not kill infections as well as does alcohol, although it is usually mild enough such as not to irritate the ear.

Also commonly used to clean pet ears is a mixture of acetic acid and water, or acetic acid and alcohol. While such mixtures are effective in killing bacteria and in eliminating yeast infections, they are not pH balanced and may irritate or actually burn the ear if the pH is too low. Additionally, the acetic acid/water mixture does not contain a drying agent, while the acetic acid/alcohol mixture has a tendency to over-dry to ear.

Attention is called to U.S. Pat. No. 4,169,065 (Robertson) which describes an ear cleaning solution especially for dogs containing a mixture of alcohol, acetic acid, hydrogen peroxide and soap in a water base. The mixture in question is intended to be applied directly to the ear and down to the ear drum, with the excess either blotted out or shaken out by the dog, with any remaining residue being harmless.

Robertson claims that his invention properly cleans pet's ears by having a solvent for the oils, alcohol; an emulsifier, soap, to lower the surface tension of the dissolved materials thereby keeping the mixture and the dissolved waxes and oils in the ear in solution; a scrubber, hydrogen peroxide, which in cooperation with the soap forms bubbles which act to aid mechanically in the removal of oils and waxes; and a solvent for the waxes, acetic acid, that changes the pH to slightly acidic and which also has anti-bacterial effects. Robertson also claims that the invention does not need to be rinsed or flushed out of the ear.

However, if Robertson's invention is used too frequently, the mixture may leave the ear too dry and irritated. Robertson suggests two different concentrations of his mixture, one for weekly use and one for daily use, to avoid this problem, but this does not eliminate the problem.

U.S. Pat. No. 4,769,171 (Harless) describes a liquid ear cleansing composition with a pH of about 1.9 to 2.7 which includes an acid buffer system. Harless describes the solution as including propylene glycol as a solvent, as well as a thickening agent and a surface active agent. Harless claims his invention is effective against yeast infections, in dissolving ear wax and as a carrier material for topical application of antibiotics and steroids.

The Harless solution is claimed to be pH balanced to a pH of about 1.9 to 2.7. According to Harless, controlling the pH is important as a low pH will irritate the ear, while a pH that is too high will not be effective against the yeast organism. The present invention is pH balanced to a pH of from 1.8 to 6.6 because of the fact that the pH of most pet skin is of about 6.2 to 7.2, and that in order to prevent irritation of the ear or skin from a solution that is too acidic, the pH needs to be adjusted upward to a point where the irritation is minimal or nonexistent, while still being effective against microorganisms, including yeast.

Harless further claims that his solution is sufficiently viscous to stay in the ear for a sufficient time to properly treat yeast infections stating that traditional solutions are too runny to be effective. Harless describes his composition as having a syrupy, oily or pasty consistency by using a thickening agent such as carboxymethylcellulose. However, by making the solution viscous, the solution stays in the ear, thereby attracting dirt and dust particles and the like, and further contributing to problems associated with moist ears. Furthermore, a viscous solution is not easily cleaned out of the ear or shaken out by the pet.

The present invention is liquid, and should remain in the ear or on the skin about 5 minutes after application. All that is required to achieve this is to apply a small amount in the pet's ear or on the skin, and when applying to the ear, to gently rub the outside of the ear while holding the pet's head, thereby allowing the solution to have its desired effect. In the case of application in the ear, the canal may be occluded with a small amount of cotton during this process to protect against drenching should the pet shake its head. Once the solution has been left in the ear or on the skin for the prescribed period of time, the pet may be let loose. In the case of application in the ear, the pet may shake its head, thereby removing any excess solution in the ear canal, then cotton may be used to blot any solution remaining in the ear or to assist in cleaning. The present invention is also designed not to have any harmful effects if not completely removed from the ear, as the solution is not viscous and will evaporate out of the ear without leaving any residual film in the ear which is likely to attract foreign particles.

The present invention relates to a novel multi-purpose cleansing solution of acetic acid and boric acid with a solvent and a non-ionic surfactant in a water base for use on pets for the routine cleaning of the ear, the cleaning of the sensitive ear, particularly for cleaning moist, waxy or odiferous ears, the prevention and treatment of ear disease, including the elimination of ear mites, acidification of the ear, and wound cleaning. The present invention includes a drying agent such that any excess solution remaining after treatment does not have any adverse effects. The present invention preferably contains a humectant such as glycerin to soothe the area being treated, and is preferably pH balanced to avoid any burning or irritation from the solution. The present invention can be combined with a topical anesthetic to provide relief from pain caused by irritation, redness, swelling and lesions while the pet is being treated. Additionally, the solution may be used as a carrier material for topical applications of medications including corticosteroids and antibiotics.

DETAILED DESCRIPTION OF THE INVENTION

Keeping a pet's ears clean and free from infection and parasites is difficult because the structure of most pet ears do not allow access for cleaning as the structure of the ear canal of pets are convoluted and inverted, and furthermore, pet ears are not self-cleaning or draining, and naturally produce oils and lipids, or fatty acids, and wax, collectively called cerumen, which means that they are prone to becoming irritated because of wax build-up, excessive moisture or yeast infections. Excessive moisture in the ear allows organisms commonly found in the ear canal to grow in disproportionate numbers.

The present invention discloses a novel multi-purpose cleansing solution of acetic acid and boric acid in a water base. The preferred embodiment contains a solvent such as propylene glycol and a non-ionic surfactant such as a polysorbate. Furthermore, the solution contains a humectant such as glycerin to soothe the area being treated, and is preferably pH balanced to avoid burning the area being treated. Additionally, as applied to the ears, the present invention is not ototoxic.

Acetic acid has antimicrobial capacities and is effective at various percentages against pseudomonas (the cause of Swimmer's Ear), staphylococcus, streptococcus and various yeasts. Boric acid is effective as an insecticide and a drying agent, and is antibacterial and antifungal. Furthermore, both acetic acid and boric acid act as acidifying agents and will also together dry the area being treated. Acetic acid preferably comprises from about 0.5%–5.0% of the present composition, and boric acid preferably comprises from about 0.5% to 5.0% of the present composition.

The addition of a solvent such as propylene glycol acts as a surfactant and assists in penetration, contact, absorption and cleaning, and as propylene glycol is water-soluble, it does not leave a residue after it has been applied.

The addition of a non-ionic surfactant provides a surface acting agent which lowers the surface tension, and therefore makes debris more easily dispersed. In the preferred embodiment, the non-ionic surfactant is a polysorbate.

The preferred embodiment also contains a humectant such as glycerin to soothe the area being treated.

The present composition is preferably pH balanced by the addition of a base such as triethanolamine, to elevate the pH to about 1.8 to 6.6, keeping in mind that the pH of pet skin is of about 6.2 to 7.2, and that in order to prevent irritation of the ear or skin from a solution that is too acidic, the pH needs to be adjusted upward to a point where the irritation is minimal or nonexistent, while still being effective against microorganisms, including yeast.

The solution is therefore anti-yeast, the most common culprit in ear problems, anti-mite, antimicrobial, and antibacterial. The solution specifically controls pseudomonas, the cause of Swimmer's Ear, staphylococcus, streptococcus, and inhibits the growth of other less frequently found organisms. It helps to eliminate wax, dries and acidifies the ear canal, as an acidic environment is fatal to yeast organisms.

The present composition may also include a topical anesthetic such as lidocaine hydrochloride to provide relief from pain while the pet is being treated. Lidocaine hydrochloride preferably comprises about 0.1 to 4.0% of the present composition. The solution is also effective when combined with corticosteroids to reduce inflammation or antibiotics to eliminate more persistent or serious infections, while still acidifying the ear.

For application of the solution to clean pet ears, approximately one (1) teaspoon (5 ml) of the solution is applied directly into the pet's ear canal and massaged thoroughly. The canal may be occluded with a small amount of cotton during this process to protect against drenching should the pet shake its head. For maximum benefit, the solution should remain in the ear at least 5 minutes before attempting to manually clean. The ear is then cleaned by stuffing wads or balls of cotton in the ear and massaging so the debris sticks to the cotton. An applicator stick may be of assistance where repetitive cleaning is required. In dry and/or irritated ears with little debris and/or wax, the cotton may become irritating. In this case, a tiny bulb or a water pick can be helpful. Any excess solution can then be blotted out, any solution remaining in the ear not being harmful.

What is claimed is:

1. A composition comprising a water base, a solvent, a non-ionic surfactant, acetic acid in the range of from about 0.5–5.0% by volume, and boric acid in the range of from about 0.5– 5.0% by volume.

2. A composition as claimed in 1, further including a humectant.

3. A composition as claimed in 1, wherein said solvent is propylene glycol.

4. A composition as claimed in 1, wherein said non-ionic surfactant is a polysorbate.

5. A composition as claimed in 2, wherein said humectant is glycerin.

6. A composition as claimed in 2, wherein the composition is pH balanced to from 1.8–6.6.

7. A composition as claimed in 6, wherein triethanolamine is added to elevate the pH.

8. A composition as claimed in 2, wherein a topical anesthetic is added.

9. A composition as claimed in 8, wherein said topical anesthetic is lidocaine hydrochloride in the range of about 0.1 to 4.0% by volume.

* * * * *